United States Patent
Ehlhardt et al.

(10) Patent No.: US 6,174,921 B1
(45) Date of Patent: Jan. 16, 2001

(54) ANTITUMOR COMPOSITIONS AND METHODS OF TREATMENT

(75) Inventors: William J Ehlhardt, Indianapolis; James E Ray, Indinapolis; John E Toth, Indianapolis, all of IN (US)

(73) Assignee: Eli Lilly and Company, Indianapolis, IN (US)

( * ) Notice: Under 35 U.S.C. 154(b), the term of this patent shall be extended for 0 days.

(21) Appl. No.: 09/269,698

(22) PCT Filed: Oct. 2, 1997

(86) PCT No.: PCT/US97/15847

§ 371 Date: Mar. 18, 1999

§ 102(e) Date: Mar. 18, 1999

(87) PCT Pub. No.: WO98/14185

PCT Pub. Date: Apr. 9, 1998

Related U.S. Application Data

(60) Provisional application No. 60/027,836, filed on Oct. 4, 1996.

(51) Int. Cl.[7] .......................... A61K 31/64; C07C 307/10
(52) U.S. Cl. ............................... 514/592; 564/39; 564/42
(58) Field of Search ............................ 514/592; 564/39, 564/42, 64

(56) References Cited

U.S. PATENT DOCUMENTS

| | | |
|---|---|---|
| 3,418,367 | 12/1968 | Dietrich, et al. . |
| 4,845,128 | 7/1989 | Harper, et al. . |
| 5,216,026 | 6/1993 | Howbert . |

OTHER PUBLICATIONS

Hayman. D.F. Hypoglycaemic agents, J. Pharm. Pharmacol., 1964, vol. 16, pp. 538–548, especially p. 542.

*Primary Examiner*—Shailendra Kumar
(74) *Attorney, Agent, or Firm*—Paul J. Gaylo

(57) ABSTRACT

This invention provides certain substituted benzenesulfonamide derivatives and methods for using them in the treatment of susceptible neoplasms in mammals. Also provided are certain novel pharmaceutical formulations employing these benzenesulfonamide derivatives in combination with a carrier.

3 Claims, No Drawings

ANTITUMOR COMPOSITIONS AND METHODS OF TREATMENT

This application is a continuation of provisional application No. 60/027,836, filed Oct. 4, 1996, and a 371 of PCT/US97/15847, filed Oct. 2, 1997.

BACKGROUND OF THE INVENTION

In recent years fundamental advances have been made in the development of chemical agents and regimens of therapy to combat neoplastic diseases. Despite these continuing advances, cancers continue to exact intolerable levels of human pain and suffering. The need for new and better methods of treating neoplasms and leukemias continues to fuel efforts to find new classes of antitumor compounds, especially in the area of inoperable or metastatic solid tumors, such as the various forms of lung cancer. Of the one million new cases of cancer diagnosed in the United States each year, more than 90% represent non-hematopoetic tumors, where improvements in five-year survival rates have been modest, at best. B. E. Henderson, et al., *Science*, 254:1131–1137 (1991).

The recent avalanche of information regarding the basic biological processes involved in neoplasms has led to a deeper understanding of the heterogeneity of tumors. Ongoing work has led to the realization that individual tumors may contain many subpopulations of neoplastic cells that differ in crucial characteristics, such as karyotype, morphology, immunogenicity, growth rate, capacity to metastasize, and response to antineoplastic agents.

It is because of this extreme heterogeneity among populations of neoplastic cells that new chemotherapeutic agents should have a wide spectrum of activity and a large therapeutic index. In addition, such agents must be chemically stable and compatible with other agents. It is also important that any chemotherapeutic regimen be as convenient and painless as possible to the patient.

This invention reports a series of novel sulfonylureas that are useful in the treatment of solid tumors. These compounds are orally active—which, of course, results in less trauma to the patient—and are relatively non-toxic. These compounds also have an excellent therapeutic index. The compounds and their formulations are novel.

Many sulfonylureas are known in the art. Certain of these compounds are known to have hypoglycemic activities, and have been used medicinally as such agents. In addition, some sulfonylureas have been taught to have herbicidal and antimycotic activities. General reviews of compounds of this structural type are taught by Kurzer, *Chemical Reviews*, 50:1 (1952) and C. R. Kahn and Y. Shechter, *Goodman and Gilman's. The Pharmacological Basis of Therapeutics*, (Gilman, et al., 8th ed. 1990) 1484–1487.

Some diarylsulfonylureas have been reported as being active antitumor agents. e.g., U.S. Pat. No. 5,169,860, of F. Mohamadi and M. Spees, issued Dec. 8, 1992; U.S. Pat. No. 4,845,128 of Harper, et al., issued Jul. 4, 1989; U.S. Pat. No. 5,110,830 of Harper, et al., issued May 5, 1992; U.S. Pat. No. 5,116,874 of G. A. Poore, issued May 26, 1992; U.S. Pat. No. 5,216,026, of J. Howbert, issued Jun. 1, 1993; U.S. Pat. No. 5,216,027, of J. E. Ray, et al., issued Jun. 1, 1993; U.S. Pat. No. 5,260,338, of R. W. Harper, et al., issued Nov. 9, 1993; U.S. Pat. No. 5,594,028, of R. W. Harper, et al., issued Jan. 14, 1997; U.S. Pat. No. 5,302,724, of J. J. Howbert, et al., issued Apr. 12, 1994; U.S. Pat. No. 5,270,329, of W. L. Scott, et al., issued Dec. 14, 1993; U.S. Pat. No. 5,234,955, of J. E. Ray, et al., issued Aug. 10, 1993; U.S. Pat. No. 5,354,778, of J. E. Ray, et al., issued Oct. 11, 1994; U.S. Pat. No. 5,258,406, of J. E. Toth, et al., issued Nov. 2, 1993; U.S. Pat. No. 5,262,440, of W. J. Ehlhardt, et al., issued Nov. 16, 1993; U.S. Pat. No. 5,254,582, of G. B. Boder, et al., issued Oct. 19, 1993; U.S. Pat. No. 5,565,494, of G. B. Grindey, et al., issued Oct. 15, 1996; U.S. Pat. No. 5,387,681, of W. D. Miller, et al., issued Feb. 7, 1995; and U.S. Pat. No. 5,529,999, of J. E. Ray, et al., issued Jun. 25, 1996; the entirety of all of which are herein incorporated by reference.

SUMMARY OF THE INVENTION

This invention provides novel compounds of Formula I

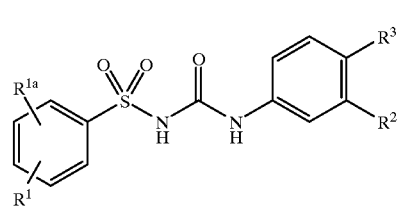

wherein:

$R^1$ is $C_2$–$C_8$ alkenyl;

$R^{1a}$ is hydrogen or hydroxy; and $R^2$ and $R^3$ are independently selected from the group consisting of hydrogen, halo, $C_1$–$C_6$ alkyl, and trifluoromethyl, provided that no more than one of $R^2$ and $R^3$ can be hydrogen;

or a pharmaceutically acceptable salt, solvate, or prodrug thereof.

This invention also provides a method of treating a susceptible neoplasm in a mammal which comprises administering to a mammal in need of said treatment an effective amount for treating a susceptible neoplasm of a compound of Formula I.

In addition, this invention provides pharmaceutical formulations comprising an effective amount for treating susceptible neoplasms of a compound of Formula I, or a salt, solvate or prodrug thereof, in combination with a suitable pharmaceutical carrier, diluent, or excipient. These formulations are useful in the treatment of mammals suffering from susceptible neoplasms.

DETAILED DESCRIPTION AND PREFERRED EMBODIMENTS

As used herein, the term "halo" refers to fluoro, chloro, bromo, and iodo. The term "$C_1$–$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl.

The term "$C_2$–$C_8$ alkenyl" as used herein represents a straight or branched, monovalent, unsaturated aliphatic chain having from two to eight carbon atoms. Typical $C_2$–$C_8$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 1-butenyl, 2-pentenyl, and the like.

Preferred methods of treatment employ compounds of Formula I in which $R^1$ is ethenyl or propenyl; and $R^2$ and $R^3$ are independently selected from the group consisting of hydrogen, chloro, fluoro, bromo, iodo, methyl, ethyl, and trifluoromethyl.

The compounds of Formulas I are generally referred to as derivatives of N-[[(substituted phenyl)amino]carbonyl]-(alkenylbenzene)sulfonamides. Alternatively, the compounds can be referred to as 1-(substituted phenyl)-3-(substituted phenylsulfonyl)ureas or N- and N'-substituted sulfonylureas.

The compounds of Formulas I can be prepared by methods known in the literature. Generally, these methods involve either the reaction of a sulfonamide with an isocyanate, a reaction of a sulfonylisocyanate with an appropriately substituted aniline, or a reaction of a sulfonylcarbamate with an appropriately-substituted aniline.

A preferred process for preparing a compound of Formula I comprises reacting a sulfonylisocyanate of Formula II

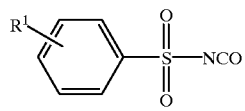

with an aniline derivative of Formula III

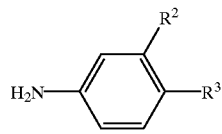

where $R^1$, $R^2$, and $R^3$ are the same as previously defined.

The reaction between compounds II and III is usually performed using equimolar amounts of the two reactants, although other ratios are operative. The reaction is preferably carried out in a solvent which is nonreactive under the reaction conditions such as benzene, toluene, acetonitrile, diethyl ether, tetrahydrofuran, dioxane, methylene chloride, or acetone.

The reaction can be carried out at temperatures from about 0° C. up to about 100° C. At the preferred temperature range of from about 20° C. to about 30° C., the reaction produces a strong exotherm and the reaction is usually complete within one hour. The product thus obtained is recovered by filtration and can be purified, if desired, by any number of methods known to those skilled in the art, such as chromatography or crystallization.

An alternative preferred process for preparing a compound of Formula I comprises reacting an appropriately substituted sulfonamide of Formula IV

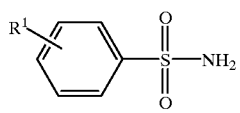

with an isocyanate of Formula V

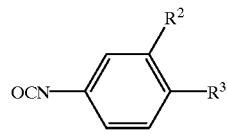

to provide the corresponding compound of Formula I.

The reaction is generally performed in a mixture of water and a water-miscible, non-reactive solvent such as tetrahydrofuran or acetone in the presence of a base such as sodium hydroxide, potassium hydroxide, lithium hydroxide, sodium methoxide, sodium hydride and the like. Generally, an equimolar or slight molar excess of V is employed, although other ratios are operative. Usually, the amount of base used is approximately equimolar to the amount of IV. The reaction is generally carried out from about 0° C. up to about 100° C. At the preferred temperature of about 20° C. to about 30° C., the reaction is usually complete within about three hours.

A preferred process for preparing a compound of Formula I involves reacting a sulfonamide of Formula IV with an alkyl haloformate of the formula $XCOOR^4$, where X is bromo or chloro and $R^4$ is $C_1$–$C_3$ alkyl, to provide the carbamate of Formula VI and then reacting it with an aniline derivative of Formula III to provide the corresponding product of Formula I.

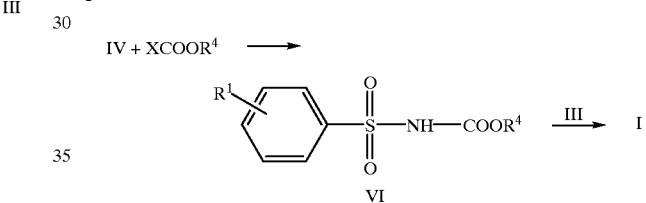

The transformation of IV into VI is usually accomplished in a non-reactive solvent, such as acetone or methyl ethyl ketone, in the presence of an acid scavenger, such as an alkali metal carbonate, for example potassium carbonate. A molar excess of the haloformate is usually added, although other ratios are operative. The reaction mixture is heated to a temperature from about 30° C. up to the reflux temperature of the mixture for a period of about 1–6 hours to provide the desired intermediate VI. Intermediate carbamate VI and the substituted aniline III are then heated together in an inert high-boiling solvent, such as dioxane, toluene, or diglyme, at temperatures from about 50° C. up to the reflux temperature of the mixture to provide the desired product of Formula I.

The carbamate of Formula VI can also be synthesized by the procedure described by Atkins and Burgess. G. Atkins and E. Burgess, *Journal of the American Chemical Society*, 94:6135 (1972). In this process triethylamine and a substituted aniline are mixed in the presence of a solvent such as benzene. To this mixture a sulfamoyl chloride is added to produce the carbamate of Formula VI.

Intermediates II, III, IV, V, and VI, and any other reagents required for these methods of preparation are commercially available, are known in the literature, or can be prepared by methods known in the art.

This invention encompasses the pharmaceutically acceptable salts of the compounds defined by Formula I. Although generally neutral, a compound of this invention can possess a sufficiently acidic functional group, and accordingly react with any of a number of organic or inorganic bases to form a pharmaceutically acceptable salt.

The term "pharmaceutically acceptable salt" as used herein, refers to salts of the compounds of Formula I which are substantially non-toxic to living organisms. Typical pharmaceutically acceptable salts include those salts prepared by reaction of the compounds of the present invention with a pharmaceutically acceptable organic or inorganic base. Such salts are known as base addition salts.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred. Organic bases can also be used, including primary, secondary, and tertiary alkyl amines such as methylamine, triethylamine, and the like.

It should be recognized that the particular counterion forming a part of any salt of this invention is not of a critical nature, so long as the salt as a whole is pharmacologically acceptable and as long as the counterion does not contribute undesired qualities to the salt as a whole.

This invention further embraces the pharmaceutically acceptable solvates of the compounds of Formulas I. The Formula I compounds can combine with solvents such as water, methanol, ethanol and acetonitrile to form pharmaceutically acceptable solvates such as the corresponding hydrate, methanolate, ethanolate and acetonitrilate.

This invention also encompasses the pharmaceutically acceptable prodrugs of the compounds of Formula I. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, or improved systemic stability (an increase in plasma half-life, for example).

Typically, such chemical modifications include:

1) ester or amide derivatives which may be cleaved by esterases or lipases;

2) peptides which may be recognized by specific or nonspecific proteases; or 3) derivatives that accumulate at a site of action through membrane selection of a prodrug form or a modified prodrug form; or any combination of 1 to 3, supra. Conventional procedures for the selection and preparation of suitable prodrug derivatives are described, for example, in H, Bundgaard, *Design of Prodrugs,* (1985).

The terms and abbreviations used in the instant examples have their normal meanings unless otherwise designated. For example "_C" refers to degrees Celsius; "N" refers to normal or normality; "mmole" refers to millimole; "g" refers to gram or grams; "ml" means milliliter or milliliters; "M" refers to molar or molarity; "FDMS" refers to field desorption mass spectrometry; "m.p." refers to melting point; and "NMR" refers to nuclear magnetic resonance.

The following examples further illustrate the preparation of the compounds of Formula I. These examples are illustrative only and are not intended to limit the scope of the invention in any way.

EXAMPLE 1
Preparation of N-[[(4-chlorophenyl)amino]carbonyl]-4-(ethenyl)benzenesulfonamide

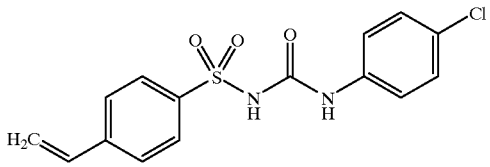

To a solution of 4-vinylbenzenesulfonamide, prepared essentially as described in R. H. Wiley, et al., *Journal of the American Chemical Society,* 78:2169 (1956), (5.1 g, 28 mmol) in 1N aqueous sodium hydroxide solution (28 ml) and acetone (14 ml) was added, dropwise, a solution of 4-chlorophenylisocyanate (4.3 g, 28 mmoles) in acetone (14 ml) over 10 minutes. Two hours later the mixture was filtered and the filtrate treated with 1N hydrochloric acid (28 ml). The resulting solid was collected by filtration and rinsed with water (100 ml). The crude product was purified by dissolving in 100 ml water containing 40 ml 1N sodium hydroxide, followed by filtration of insoluble material and neutralization with 40 ml 1N hydrochloric acid. After filtration and washing (200 ml of water), vacuum drying gave 4.9 g (52%) of the purified title sulfonylurea.

Analysis of the product gave the following results: mp=182–184° C.; $R_f(9/1, CHCl_3/MeOH)=0.30$; $^1H$ NMR (300 MHz, $d_6$-DMSO) δ 5.45 (d, 1H, J=10.9 Hz, C$\underline{H}$), 5.98 (d, 1H, J=17.6 Hz, C$\underline{H}$), 6.83(dd, 1H, J=10.9,17.6 Hz, C$\underline{H}$), 7.2–7.4 (m, 4H, Ar—$\underline{H}$), 7.68 (d, 2H, J=8.3 Hz, Ar—$\underline{H}$), 7.89 (d, 2H, J=8.3 Hz, Ar—$\underline{H}$), 9.0 (s, 1H, exchanges with $D_2O$, N$\underline{H}$) and 10.9 (bs, 1H, exchanges with $D_2O$, $SO_2N\underline{H}$); IR(KBr) 3360, 1710, 1604, 1542, 1462, 1340, 1161, 1034 and 927 cm$^{-1}$; UV(EtOH) $\lambda_{max}(\epsilon)$ 251.2 (33271) and 204.4 (36099) nm; FDMS (MeOH) m/e 336, 338(M$^+$).

Analysis for $C_{15}H_{13}ClN_2O_3S$:
Theory: C, 53.49; H, 3.89; N, 8.32.
Found: C, 53.54; H, 3.96; N, 8.19.

EXAMPLE 2
Preparation of N-[[(3,4-dichlorophenyl)amino]carbonyl]-4-(ethenyl)benzenesulfonamide

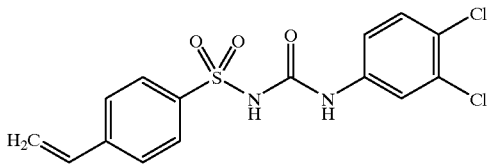

The procedure of Example 1 was followed, using 4-vinylbenzenesulfonamide (10 g, 55 mmoles), 1N sodium hydroxide (55 ml) and 3,4-dichlorophenylisocyanate (97%, 11 g, 55 mmoles). The crude product was purified by stirring in ethanol (50 ml) for 30 minutes, followed by filtration and vacuum drying to give 8.4 g (41%) of the title sulfonylurea.

Analysis of the product gave the following results: mp=179° C.; $R_f(9/1, CHCl_3/MeOH)=0.24$; $^1H$ NMR (300 MHz, $d_6$-DMSO) δ 5.45 (d, 1H, J=10.9 Hz, C$\underline{H}$), 5.98 (d, 1H, J=17.6 Hz, C$\underline{H}$), 6.83(dd, 1H, J=10.9, 17.6 Hz, C$\underline{H}$), 7.25 (m, 1H, Ar—$\underline{H}$), 7.43 (d, 1H, J=8.7 Hz, Ar—$\underline{H}$), 7.6–7.7 (m, 3H, Ar—$\underline{H}$), 7.86 (d, 2H, J=8.7 Hz, Ar—$\underline{H}$), 9.1 (s, 1H, exchanges with $D_2O$, N$\underline{H}$) and 11.0 (bs, 1H, exchanges with $D_2O$, $SO_2N\underline{H}$); IR(KBr) 3347, 3250, 1710, 1589, 1521, 1464, 1338, 1161, 1040 and 843 cm$^{-1}$;

EXAMPLE 3

Preparation of N-[[(4-chlorophenyl)amino]carbonyl]-3-(ethenyl)benzenesulfonamide

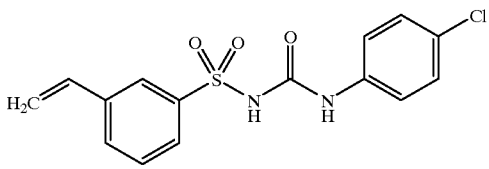

The 3-vinylbenzenesulfonamide was prepared by reacting a solution of 3-bromobenzenesulfonamide (24 g, 100 mmoles) with vinyltributyltin (97%, 35 ml, 116 mmoles) in the presence of tetrakis(triphenylphosphine)palladium(0) (2.3 g, 2 mmoles) in toluene (200 ml) and heated under nitrogen at reflux for 90 minutes. After cooling and filtering through CELITE®, the reaction mixture was evaporated to yield 50 g of yellow solid. Chromatography (silica gel, 100% hexanes to 40% ethyl acetate/hexane) provided 5.2 g (28%) of the 3-vinylbenzenesulfonamide. Recrystallization from methanol gave an analytical sample.

Analysis of the product gave the following results: mp=131–132° C.; $R_f$(1/1, EtOAc/hexane)=0.48; $^1$H NMR (300 MHz, $d_6$-DMSO) δ 5.38 (d, 1H, J=10.9 Hz, C$\underline{H}$), 5.89 (d, 1H, J=17.6 Hz, C$\underline{H}$), 6.83(dd, 1H, J=10.9,17.6 Hz, C$\underline{H}$), 7.35 (s, 2H, SO$_2$N$\underline{H_2}$), 7.50 (m, 1H, Ar—$\underline{H}$), 7.7 (m, 2H, Ar—$\underline{H}$) and 7.89 (s, 1H, Ar—$\underline{H}$); IR(KBr) 3333, 3246, 1557, 1328, 1158, and 890 cm$^{-1}$; UV(tOH) $\lambda_{max}$(ε) 297.8 (452), 288.6 (730), 280.8 (763), 248.2 (11423) and 214.8 (25659) nm; FDMS (MeOH) m/e 183(M$^+$).

Analysis for $C_8H_9NO_2S$:

Theory: C, 49.62; H, 4.95; N, 7.64.

Found: C, 49.90; H, 4.61; N, 7.32.

The title compound was prepared essentially as described in Example 1, using the 3-vinylbenzenesulfonamide (3.0 g, 16.4 mmoles) prepared supra, 4-chlorophenylisocyanate (2.6 g, 16.6 mmoles) and 1N sodium hydroxide (16.4 ml). The crude product was chromatographed (silica gel, 1–5% methanol in methylene chloride) to give 2.7 g (49%) of N-[[(4-chlorophenyl)amino]carbonyl]-3-(ethenyl)benzenesulfonamide.

Analysis of the product gave the following results: mp=153–154° C.; $R_f$(9/1, CHCl$_3$/MeOH)=0.15; $^1$H NMR (300 MHz, $d_6$-DMSO) δ 5.38 (d, 1H, J=10.9 Hz, C$\underline{H}$), 5.89 (d, 1H, J=17.6 Hz, C$\underline{H}$), 6.83(dd, 1H, J=10.9,17.6 Hz, C$\underline{H}$), 7.25–7.40 (m, 4H, Ar—$\underline{H}$), 7.58 (m, 1H, Ar—$\underline{H}$), 7.78–7.85 (m, 2H, Ar—$\underline{H}$), 7.97 (s, 1H, Ar—$\underline{H}$), 9.1 (s, 1H, exchanges with D$_2$O, N$\underline{H}$) and 10.8 (bs, 1H, exchanges with D$_2$O, SO$_2$N$\underline{H}$); IR(KBr) 3329, 3239, 1705, 1598, 1534, 1456, 1337, 1158, 1038 and 927 cm$^{-1}$; UV(EtOH) $\lambda_{max}$(ε) 247.8 (32235) and 204.2 (35716) nm; FDMS (MeOH) m/e 336, 338 (M$^{30}$). Analysis for $C_{15}H_{13}ClN_2O_3S$:

Theory: C, 53.49; H, 3.89; N, 8.32.

Found: C, 53.45; H, 3.98; N, 8.20.

UV(EtOH) $\lambda_{max}$(ε) 254.0 (33940) and 209.6 (41966) nm; FDMS (MeOH) m/e 370, 372, 374(M$^+$).

Analysis for $C_{15}H_{12}Cl_2N_2O_3S$:

Theory: C, 48.53; H, 3.26; N, 7.55.

Found: C, 48.34; H, 3.29; N, 7.39.

Preparation

Preparation of N-ethoxycarbonyl-4-hydroxy-3-(prop-2-en-1-yl)phenylsulfonamide

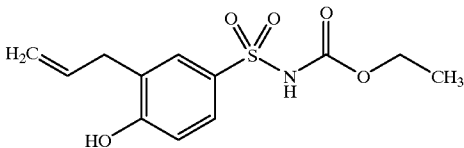

To a solution of 3-allyl-4-hydroxybenzenesulfonamide (2 g, 9.4 mM) [prepared as described in Patent Cooperation Treaty Publication WO 96/09818, published Apr. 4, 1996] in 100 ml methyl ethyl ketone was added potassium carbonate (1.4 g, 10 mM) and the mixture heated under nitrogen to reflux. After 10 minutes, ethyl chloroformate (1.8 ml, 18.8 mM, 2 equivalents) was added dropwise and the mixture refluxed for 3 hours. The cooled reaction was acidified with 1N hydrochloric acid (50 ml) and the layers separated. An additional wash with water (1×50 ml) and brine (1×24 ml), followed by drying over sodium sulfate and evaporation gave 3.3 g of the di-acylated product. The crude oil was dissolved in water (90 ml), 1N sodium hydroxide (29 ml) added and the mixture heated to reflux 2 hours. After cooling in an ice-bath, 1N hydrochloric acid (30 ml) was added and the resulting solid collected and dried to 1.87 g. Chromatography (silica gel, 100% methylene chloride to 5% methanol/methylene chloride) gave the product as a white solid, 1.3 g (49%).

Analysis of the title compound gave the following results:

$R_f$(1/9 MeOH/CHCl$_3$)=0.29; $^1$H NMR (300 MHz, DMSO-$d_6$) δ 1.05 (t, 3H, J=6.9 Hz, OCH$_2$C$\underline{H}$), 3.30 (d, 2H, J=6.7 Hz, CH$_2$=CHC$\underline{H_2}$), 3.95 (q, 2H, J=6.9 Hz, OC$\underline{H_2}$C$\underline{H_3}$), 5.05 (s, 1H, C$\underline{H_2}$=CHCH$_2$), 5.05 (d, 1H, J=4 Hz, C$\underline{H_2}$=CHCH$_2$), 5.85–5.94 (m, 1H, CH$_2$=C$\underline{H}$CH$_2$), 6.91 (d, 1H, J=8.4 Hz, Ar—$\underline{H}$), 7.50–7.60 (m, 2H, Ar—$\underline{H}$), 10.6(bs, 1H, exchanges with D$_2$O, OH), and 11.63(bs, 1H, exchanges with D$_2$O, NH); IR(KBr) 3409, 3212, 1728, 1592, 1488, 1425, 1366, 1348, 1290, 1239, 1159, 1129, 835 and 772 cm$^{-1}$; UV(EtOH) λmax(ε) 244.5 (13070) and 207.0 (31769) nm; FDMS (MeOH) m/e 285 (M$^+$).

Analysis for $C_{12}H_{15}NO_5S$:

Theory: C, 50.52; H, 5.30; N, 4.91.

Found: C, 50.39; H, 5.20; N, 4.66.

EXAMPLE 4

Preparation of N-[[[3,4-dichlorophenyl]amino]carbonyl]-4-hydroxy-3-(prop-2-en-1-yl)phenylsulfonamide

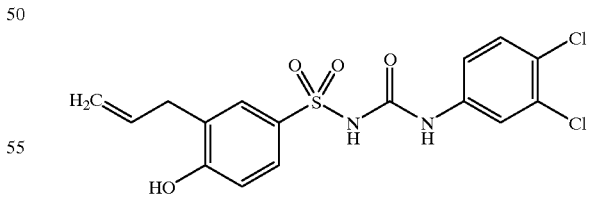

A solution of N-ethoxycarbonyl-4-hydroxy-3-(prop-2-en-1-yl)phenylsulfonamide (500 mg, 1.75 mM) and 3,4-dichloroaniline (340 mg, 2.06 mM, 1.2 equivalents) was prepared in toluene (25 ml) and heated to reflux under nitrogen, removing the toluene/ethanol azeotrope by use of a Dean-Stark trap. After 4.5 hour and removal of about 10 ml azeotrope, the solution was cooled in an ice-bath and the resulting precipitate collected and rinsed with cold toluene (10 ml). Vacuum dry to a white solid, 536 mg (76%).

Analysis of the title compound gave the following results: $R_f$ (1/9 MeOH/CHCl$_3$)=0.19; $^1$H NMR (300 MHz, DMSO-d6)δ 3.31 (d, 2H, J=6.7 Hz, CH$_2$=CHCH$_2$), 5.01 (s, 1H, CH$_2$=CHCH$_2$), 5.06 (d, 1H, J=7.9 Hz, CH$_2$=CHCH$_2$), 5.85–5.94 (m, 1H, CH$_2$=CHCH$_2$), 6.91 (d, 1H, J=8.4 Hz, Ar—H), 7.22 (m, 1H, Ar—H), 7.45 (d, 1H, J=8.8 Hz, Ar—H), 7.50–7.65 (m, 3H, Ar—H), 9.03 (bs, 1H, exchanges with D$_2$O, CONH), 10.6(bs, 1H, exchanges with D$_2$O, OH), and 10.8(bs, 1H, exchanges with D$_2$O, NH); IR(KBr) 3383, 3206, 1712, 1700, 1591, 1521, 1460, 1432, 1394, 1339, 1279, 1239, 1152, 1123, 1056, 864 and 706 cm$^{-1}$; FDMS (MeOH) m/e 400,402 (M$^+$, M$^+$+2).

Analysis for $C_{16}H_{14}Cl_2N_2O_4S$:

Theory: C, 47.89; H, 3.52; N, 6.98.
Found: C, 47.78; H, 3.61; N, 6.72.

The compounds of Formula I have been shown to be active against human tumors in vitro. The in vitro data were obtained using CCRF-CEM cells, a human leukemia cell line. Foley et al., *Cancer*, 18:522 (1965). These cells were grown using standard techniques. See, e.g., G. B. Grindey, et al., *Journal of Molecular Pharmacoloy*, 16:601 (1979). Dose-response curves were generated for various compounds to determine the concentration required for 50% inhibition of growth (IC$_{50}$). Cluster plates were prepared in duplicate with the compound at various concentrations. Test compounds were dissolved initially in DMSO at a concentration of 4 mg/ml and further diluted with solvent to the desired concentration. Cells in Roswell Park Memorial Institute 1640 media supplemented with 10% dialyzed fetal bovine serum, and 25 mM HEPES buffer were added to the well at a final concentration of 4.8×10$^4$ cells/well in a total volume of 2.0 ml. After 72 hours of incubation (95% air, 5% CO$_2$), cell numbers were determined on a ZBI Coulter counter. Cell number for indicated controls at the end of incubation was usually (4–6)×10$^5$ cells/well. Cell viability was also measured by staining with 3-[4,5-dimethylthiazol-2-yl]-2,5-diphenyl-tetrazolium bromide (MTT) using standard techniques. R. I. Freshney, *Culture of Animal Cells: A Manual of Basic Technique*, 253–254 (2d ed. 1987).

Table I, infra, shows the results of one such in vitro screening panel. Column 1 refers to the example number of the compound tested; Column 2 depicts the in vitro cytoxicity against CCRF-CEM cells by relating the concentration of the test compound required for 50% inhibition of growth (IC$_{50}$) of the cells in the well.

TABLE I

Activity of the Compounds of Formula I Against Tumor Cells In Vitro

| Example No. | (CCRF-CEM) IC$_{50}$ μg/ml |
|---|---|
| 1 | 19.8 |
| 2 | 9.3 |
| 3 | 14.4 |
| 4 | |

The compounds of Formula I have also been shown to be active against transplanted human tumors in vivo. To demonstrate the anti-tumor activity of the compounds of Formula I, these compounds were tested in mice bearing different allograft and xenograft tumors.

One of the tumor models used for showing the antineoplastic activity of the sulfonylureas of this invention was the human colon xenograft HXGC3. J. A. Houghton and D. M. Taylor, *British Journal of Cancer*, 37:213–223 (1978). This tumor was obtained from St. Jude's Children's Research Hospital and has been widely used as a human tumor model.

A second tumor model employed C3H mice bearing the widely used allograft 6C3HED lymphosarcoma, also known as the Gardner lymphosarcoma (GLS). The 6C3HED lymphosarcoma was obtained from the Division of Cancer Treatment, National Cancer Institute, Tumor Bank, maintained at E. G. and G. Mason Research (Worcester, Mass.).

First passage tumors were stored in liquid nitrogen, using standard techniques. The transplanted tumor was reestablished from the Tumor Bank every six months or as needed. The tumor was maintained by serial passage twice weekly in the host mice.

In the procedures utilized here, the tumor was removed from passage animals and minced into 1- to 3-mm cubic fragments using sterile techniques. Tumor pieces were checked for sterility using both Antibiotic Medium 1 and Brain Heart Infusion (Difco, Detroit, Mich.). The xenograft tumor pieces were implanted into the recipient CD1 Nu/Nu mice subcutaneously in an axillary site by trochar. The allograft 6C3HED tumor pieces were implanted into the recipient C3H mice in an analogous fashion.

Drug therapy on the appropriate schedule was initiated seven days after tumor implantation for the HXGC3 xenograft and the day after tumor implantation for the 6C3HED allograft. The compound being tested was mixed with 2.5% Emulphor EL620 from GAF Corporation (1:40 dilution in 0.9% saline). The total dosage volume for each administration was 0.5 ml. All animals were weighed at the beginning and end of administration of the subject compounds. Food and water were provided ad libitum.

Each control group and each dosage level of the treated groups consisted of 9 or 10 mice selected at random from the pool of implanted animals. The formulations were administered orally by gavage with the use of an 18-gauge needle. Compounds were dosed daily for 10 days for the studies using the human tumor xenografts and 8 days for the studies using the allograft.

The xenograft tumor was measured five days after treatment ended with two dimensional measurements (width and length) of the tumor taken using digital electronic calipers interfaced to a microcomputer. J. F. Worzalla, et al., *Investigational New Drugs*, 8:241–251 (1990). The allograft was measured in a like manner the day after the dosing schedule ended. Tumor weights were calculated from these measurements using the following formula:

$$\text{Tumor weight (mg)} = \frac{\text{tumor length (mm)} \times [\text{tumor width(mm)}]^2}{2}$$

At least one control group of an equal number of mice was treated with the same volume of 2.5% Emulphor only. The percent inhibition is determined by subtracting the ratio of the mean tumor size of the test group relative to the control group from one and multiplying the result by 100.

The results of several experiments in mice bearing the HXGC3 human colon adenocarcinoma and the 6C3HED lymphosarcoma when the Formula I compounds were administered orally are provided in Table II. In the table, Column 1 refers to the example number of the compound tested; Column 2 describes the particular human tumor xenograft or mouse allograft being studied; Column 3 gives the dosage level of the compound of Formula I in milligrams per kilogram of body weight; Column 4 describes the percent inhibition of tumor growth; and Column 5 tallies the number of mice which died during the course of the experiment relative to the total number of animals in the group.

TABLE II

Activity of the Compounds of Formula I Against Allograft and Xenograft Tumors In Vivo

| Example No. | Tumor | Dosage (mg/kg) | Percent Inhibition | Toxic/Total |
|---|---|---|---|---|
| 1 | 6C3HED | 300 | 99 | 1/10 |
|   |        | 150 | 99 | 0/10 |
|   | 6C3HED | 1200 | Toxic | 10/10 |
|   |        | 600 | 100 | 2/10 |
|   |        | 300 | 100 | 1/10 |
|   |        | 150 | 97 | 0/10 |
|   |        | 75  | 66 | 0/10 |
|   |        | 37.5 | 34 | 0/10 |
| 2 | HXGC3 | 300 | 97 | 1/7 |
|   |       | 150 | 93 | 0/7 |
| 3 | 6C3HED | 300 | 83 | 0/10 |
|   |        | 150 | 60 | 0/10 |

The compounds of Formula I are usually administered in the form of pharmaceutical compositions. These compositions can be administered by a variety of routes including oral, rectal, transdermal, subcutaneous, intravenous, intramusclar, and intranasal. Such compositions are useful in treating solid tumors including carcinomas such as ovarian, non-small cell lung, gastric, pancreatic, prostate, renal cell, breast, colorectal, small cell lung, melanoma, and head and neck; and sarcomas such as Kaposi's and and rhabdomyosarcoma.

The Formula I compounds are preferably administered in the form of oral pharmaceutical compositions. Such compositions are prepared in a manner well known in the pharmaceutical art and comprise at least one active compound.

In another aspect, the present invention also includes novel pharmaceutical compositions which contain, as the active ingredient, the compounds of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

The active compounds are effective over a wide dosage range. For examples, dosages per day normally fall within the range of about 0.5 to about 600 mg/kg of body weight. In the treatment of adult humans, the range of about 1 to about 50 mg/kg, in single or divided dose, is preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way.

Typical compositions of this invention are described in the following examples:

FORMULATION EXAMPLE 1

Hard gelatin capsules containing the following ingredients are prepared:

| Ingredient | Quantity (mg/capsule) |
|---|---|
| Active Ingredient | 250.0 |
| Starch | 305.0 |
| Magnesium stearate | 5.0 |

The above ingredients are mixed and filled into hard gelatin capsules in 560 mg quantities.

FORMULATION EXAMPLE 2

A tablet formula is prepared using the ingredients below:

| Ingredient | Quantity (mg/tablet) |
|---|---|
| Active Ingredient | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

FORMULATION EXAMPLE 4

Tablets, each containing 60 mg of active ingredient, are prepared as follows:

| Ingredient | Quantity (mg/tablet) |
|---|---|
| Active Ingredient | 60.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 150 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 80 mg of medicament are made as follows:

| Ingredient | Quantity (mg/capsule) |
|---|---|
| Active Ingredient | 80.0 mg |
| Starch | 109.0 mg |
| Magnesium stearate | 1.0 mg |
| Total | 190.0 mg |

The active ingredient, cellulose, starch, and magnesium stearate are blended, passed through a No. 20 mesh U.S. sieve, and filled into hard gelatin capsules in 190 mg quantities.

FORMULATION EXAMPLE 6

Suppositories, each containing 225 mg of active ingredient are made as follows:

| Ingredient | Amount |
|---|---|
| Active Ingredient | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor | q.v. |
| Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Capsules, each containing 150 mg of medicament, are made as follows:

| Ingredient | Quantity (mg/capsule) |
|---|---|
| Active Ingredient | 150.0 mg |
| Starch | 407.0 mg |
| Magnesium stearate | 3.0 mg |
| Total | 560.0 mg |

The active ingredient, cellulose, starch, and magnesium stearate are blended, passed through a No. 20 mesh U.S. sieve, and filled into hard gelatin capsules in 560 mg quantities.

We claim:
1. A compound of the formula

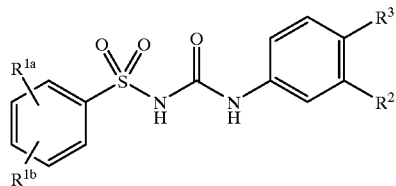

wherein:
$R^1$ is ethenyl or propenyl;
$R^{1a}$ is hydroxy;
$R^2$ is halo; and
$R^3$ is selected from the group consisting of hydrogen, halo, $C_1$–$C_6$ alkyl, and trifluoromethyl;
or a pharmaceutically acceptable salt, or solvate thereof.

2. A pharmaceutical formulation comprising an effective amount of a compound as claimed in claim 1, in combination with one or more pharmaceutically acceptable carriers, diluents, or excipients therefor.

3. A method of treating a susceptible neoplasm is a mammal which comprises administering to a mammal in need of said treatment an effective amount for treating the susceptible neoplasm of a compound as claimed in claim 1.

* * * * *